(12) United States Patent
Doan et al.

(10) Patent No.: US 9,610,454 B2
(45) Date of Patent: Apr. 4, 2017

(54) OVER TORQUE LIMITER FOR LEADLESS IMPLANTABLE MEDICAL DEVICES

(71) Applicant: PACESETTER, INC., Sylmar, CA (US)

(72) Inventors: Phong D. Doan, San Clemente, CA (US); Kavous Sahabi, Winnetka, CA (US); Arees Garabed, North Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/685,387

(22) Filed: Apr. 13, 2015

(65) Prior Publication Data

US 2016/0296761 A1    Oct. 13, 2016

(51) Int. Cl.
*A61N 1/00* (2006.01)
*A61N 1/375* (2006.01)
*F16D 7/02* (2006.01)
*A61N 1/05* (2006.01)
*A61N 1/362* (2006.01)

(52) U.S. Cl.
CPC ........... *A61N 1/3756* (2013.01); *A61N 1/057* (2013.01); *A61N 1/362* (2013.01); *F16D 7/021* (2013.01); *F16D 7/022* (2013.01); *A61N 2001/058* (2013.01)

(58) Field of Classification Search
CPC .... A61N 1/3756; A61N 1/375; A61N 1/3758; A61N 1/36; A61N 1/362; A61N 1/0558; A61N 1/057; A61N 1/0573; A61N 1/0587; A61N 1/059; A61N 2001/058; A61N 2001/0578; F16D 7/021; F16D 7/022

See application file for complete search history.

(56) References Cited

U.S. PATENT DOCUMENTS

2011/0307043 A1*  12/2011  Ollivier ............... A61N 1/0587
607/127

* cited by examiner

*Primary Examiner* — Mallika D Fairchild

(57) ABSTRACT

In accordance with one embodiment, a leadless implantable medical device (LIMD), compromises a hermetic housing that has a distal portion and proximal portion. An electrode is proximate to the distal portion. An electronics package is disposed in the housing, in which the electronics package is configured to generate and deliver stimulation signals to the electrode. A fixation mechanism is disposed on the distal portion of the housing. A torque mechanism is disposed on the proximal portion of the housing. The torque mechanism has a tool engagement element movably coupled to the housing. The tool engagement element has a rotational force applied thereto during implant. The torque mechanism includes a torque limiter that maintains a fixed relation between the tool engagement element and the housing when in an engaged state. The torque limiter changes from the engaged state to a disengaged state when the rotational force exceeds a predetermined torque limit.

16 Claims, 9 Drawing Sheets

OVER TORQUE LIMITER FOR LEADLESS IMPLANTABLE MEDICAL DEVICES

BACKGROUND OF THE INVENTION

Embodiments of the present invention generally relate to, and more particularly to implantable medical devices and more particularly to limiting over torque during active fixation.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like. Implantable medical devices (hereafter generally "implantable medical devices" or "IMDs") are configured to be implanted within patient anatomy and commonly employ one or more leads with electrodes that either receive or deliver voltage, current or other electromagnetic pulses (generally "energy") from or to an organ or tissue for diagnostic or therapeutic purposes.

More recently, leadless IMDs ("LIMDs") have been developed that are configured to be entirely implanted within a chamber of the heart through a nonsurgical procedure. Typically, an LIMD is introduced into the heart through a catheter. The LIMD includes a nonelectrical active fixation helix at the distal end, with the helix configured to be screwed into the heart wall in an area proximate to where it is desirable to deliver therapy. To implant the LIMD, a docking feature at the proximal end of the LIMD is temporarily connected to a docking cup at a distal end of the implant delivery catheter system. Once the LIMD is inserted into the heart chamber, the helix is secured to a desired point on the heart wall.

The physician seeks to ensure that the fixation helix is located against tissue of interest along the heart wall at an intended location. Once the physician confirms that the LIMD is located at an intended location, the physician rotates a knob on the implant delivery catheter (e.g. clockwise) at a number of turns to fixate/screw the fixation helix into the heart wall. Once the helix is properly fixated into tissue of the heart wall, the LIMD is released from the docking system and the implant delivery catheter system is removed from the patient.

When attaching the helix to tissue, a physician observes the LIMD through a series of fluoroscopy images while rotating the implant tool knob a predetermined or recommended number of turns. However, the process of attaching the helix by rotating the LIMD, while viewing a series of fluoroscopy images, presents a difficult or challenging procedure. As one example, it is difficult for the physician to know when the helix is embedded by a desired amount into the heart wall tissue, namely it is difficult to determine when the LIMD has been rotated enough. When too little rotation is applied, the LIMD may not be sufficiently fixated and dislodge at a later date. Alternatively, when excess rotation or over torqueing is applied, the helix may perforate the heart wall, particularly in regions where the heart wall is thin.

SUMMARY

In accordance with one embodiment, a leadless implantable medical device (LIMD), compromises a hermetic housing that has a distal portion and proximal portion. An electrode is proximate to the distal portion. An electronics package is disposed in the housing, in which the electronics package is configured to generate and deliver stimulation signals to the electrode. A fixation mechanism is disposed on the distal portion of the housing. A torque mechanism is disposed on the proximal portion of the housing. The torque mechanism has a tool engagement element movably coupled to the housing. The tool engagement element has a rotational force applied thereto during implant. The torque mechanism includes a torque limiter that maintains a fixed relation between the tool engagement element and the housing when in an engaged state. The torque limiter changes from the engaged state to a disengaged state when the rotational force exceeds a predetermined torque limit.

Optionally, the torque limiter allows rotation between the tool engagement element and the housing when the torque limiter is in the disengaged state. The torque mechanism may include a base member securely affixed to a proximal end of the housing and a post extending outward in a proximal direction from the base member. The tool engagement member may be rotatably mounted on the post, the torque limiter releasable interconnecting the tool engagement element and the base member when in the engaged and disengaged states.

Optionally, the base member may represent a gear having ratchet teeth positioned about a perimeter of the gear. To prevent relative rotation between the tool engagement member and the housing the torque limiter may fixably engage the ratchet teeth, when in an engaged state. The torque limiter may engage a sloped surface of the ratchet teeth, where the sloped surface forms an acute angle relative to a radius of the gear. The sloped surface may form an acute angle which may be relative to the radius of the gear. The sloped surface extends radially outward from a center of the gear and curves toward a direction of rotational movement of the torque limiter when in the disengaged state in which the torque limiter rotates with the tool engagement element about the gear.

Optionally, the torque mechanism may include a base member which may be securely affixed to a proximal end of the housing, wherein the torque limiter may represent a spring arm securely mounted to one of the tool engagement member and base member. The spring arm may maintain the fixed relation between the tool engagement element and base member when in the engaged state. When transitioning from the engaged state to the disengaged state in response to the rotational force exceeding the predetermined torque limit the spring arm may snappably release another of the tool engagement member and the base member.

Optionally, without damaging the tissue of interest, the predetermined torque limit may correspond to an amount of rotational force which may be sufficient to securely affix the fixation mechanism on the distal portion of the housing to tissue of interest. The tool engagement element may include a male docking surface shaped and dimensioned to securely engage a distal end of a delivery tool such that the delivery tool may apply the rotational force, thereby, causing the fixation mechanism to rotate and securely engage the tissue of interest.

Optionally, the torque limiter may constitute a spiral shaped spring having a first end attached to the tool engagement element and a second end attached to the housing. The spiral shaped spring may maintain an initial shape when in the engaged state so that it may transfer a fixed amount of motion from the tool engagement element to the housing when the rotational force is applied. The spiral shaped spring may change shape when in the disengaged state.

Optionally, the tool engagement element is rotatably mounted on a post extending from the proximal end of the housing. The tool engagement element includes an interior surface. The torque limiter may represent a spring fixedly mounted to the housing and may be located between the interior surface of the tool engagement element and a proximal end of the housing, The spring and interior surface may frictionally engage one another to prevent relative rotation there between when in the engaged state.

Optionally, a method for providing a leadless implantable medical device may comprise of providing a hermetic housing, which may have a distal portion and a proximal portion, where an electrode may be located proximate to the distal portion. An electronics package is disposed in the housing, and a fixation mechanism may be disposed on the distal portion of the housing. Disposing a torque mechanism on the proximal portion of the housing, the torque mechanism may include a tool engagement element movably coupled to the housing. A rotational force may be applied to the tool engagement element during implant. To maintain the torque mechanism in an engaged state, the tool engagement element and the housing may remain in a fixed relation with respect to one another when the rotational force may be at or below a predetermined torque limit. In a disengaged state, the tool engagement element may rotate relative to the housing when the rotational force exceeds the predetermined torque limit.

Optionally, comprising may provide a torque limiter, in the torque mechanism, which may allow rotation between the tool engagement element and the housing when the torque limiter is in the disengaged state. The torque mechanism may include a base member securely affixed to a proximal end of the housing, the method comprising releasable interconnecting the tool engagement element and the base member when in the engaged and disengaged states.

Optionally, the base member may represent a gear having ratchet teeth positioned about a perimeter of the gear, the method comprising preventing relative rotation between the tool engagement member and the housing by fixably engaging the ratchet teeth when in the engaged state. The predetermined torque limit may correspond to an amount of rotational force sufficient to securely affix the fixation mechanism on the distal portion of the housing to the tissue of interest, without damaging the tissue of interest.

Optionally, comprising securely engaging a docking surface on the tool engagement element with a distal end of a delivery tool and applying the rotational force through the delivery tool to cause the fixation mechanism to rotate and securely engage the tissue of interest.

DETAILED DESCRIPTION

In accordance with embodiments herein, a torque mechanism is provided on an LIMD to prevent over torque of the LIMD during implant. Initially, the torque mechanism is in an engaged state to transfer rotation from a delivery tool to the LIMD. The torque mechanism changes from an engaged state to a disengaged state when excessive rotational force is applied during implant of the LIMD. When the torque mechanism changes to a disengaged state, the delivery tool is permitted to rotate relative to the LIMD, such that even when the delivery tool continues to rotate, the LIMD will not further rotate a fixation mechanism into the heart wall. In accordance with embodiments herein, the torque mechanism includes upper and lower elements that maintain a fixed relation relative to one another when rotational forces below a predetermined torque limit are applied to the upper element. Once rotational forces, applied to the upper element, exceed the predetermined torque limit, the upper and lower elements change to a disengaged state and rotate relative to one another, thereby preventing further direct transfer of rotational forces from the delivery tool to the fixation helix or other mechanism on the distal end of the LIMD. By preventing over torque of the LIMD, embodiments herein prevent heart perforation or other damage to the heart wall. Additionally, in accordance with embodiments herein, the torque mechanism is provided with a low profile to avoid unduly increasing an overall size of the LIMD.

Figure 1A:
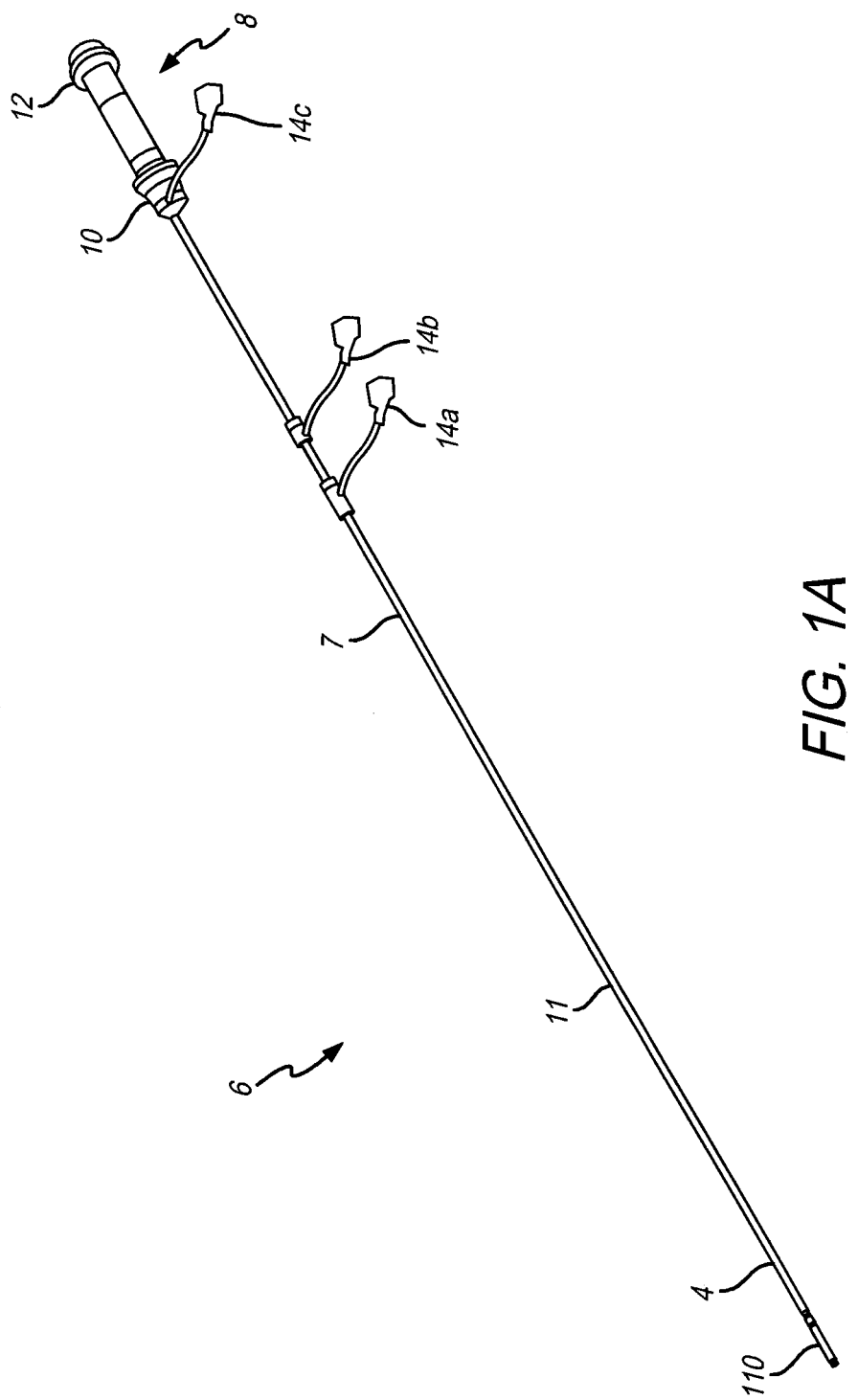
FIG. 1A illustrates a perspective view of a delivery system for delivering an LIMD into a patient, according to an embodiment of the present disclosure.

FIG. 1A illustrates a perspective view of a delivery system 6 for delivering an LIMD 110 into a patient, according to an embodiment of the present disclosure. The delivery system 6 may include an LIMD sheath 4, a guide catheter 11, an introducer sheath 7, a handle 8, a deflection knob 10, a tether shuttle 12, and flush ports 14a, 14b, and 14c. The deflection knob 10 may be used to steer and guide the catheter 11 during implantation and/or removal of the LIMD 110. The flush ports 14a, 14b, and 14c may be used to flush saline or other fluids through the catheter 11. The introducer sheath 7 may be advanced distally over the catheter 11 to provide additional steering and support for the catheter 11 during implantation and to surround the LIMD 110 as it is introduced through a trocar or introducer into a patient.

Figure 1B:
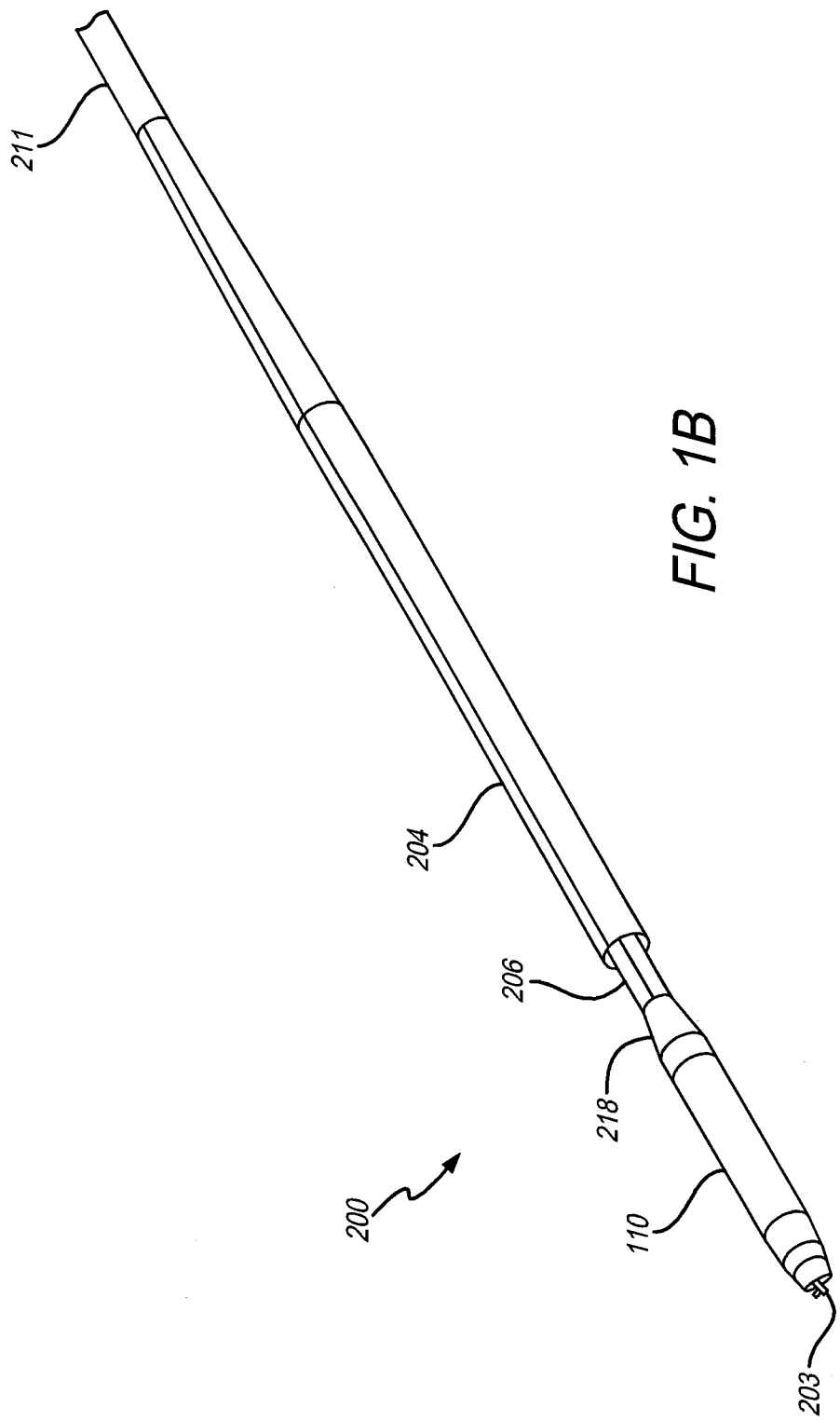
FIG. 1B illustrate a perspective view of a distal portion of an alternative delivery system and an LIMD, according to an embodiment of the present disclosure.

FIG. 1B illustrate a perspective view of a distal portion of an alternative delivery system 200 and an LIMD 110, according to an embodiment of the present disclosure. The LIMD 200 may include a helix 203 that may be used to attach the LIMD 200 to tissue of a patient. The LIMD 110 may include an attachment member that is configured to removably connect to a docking cap 218 of a catheter 206. An LIMD sheath 204 is shown pulled back proximally along the catheter 206 and a guide shaft 211 to expose the LIMD 110 and the helix 203.

Figure 1C:
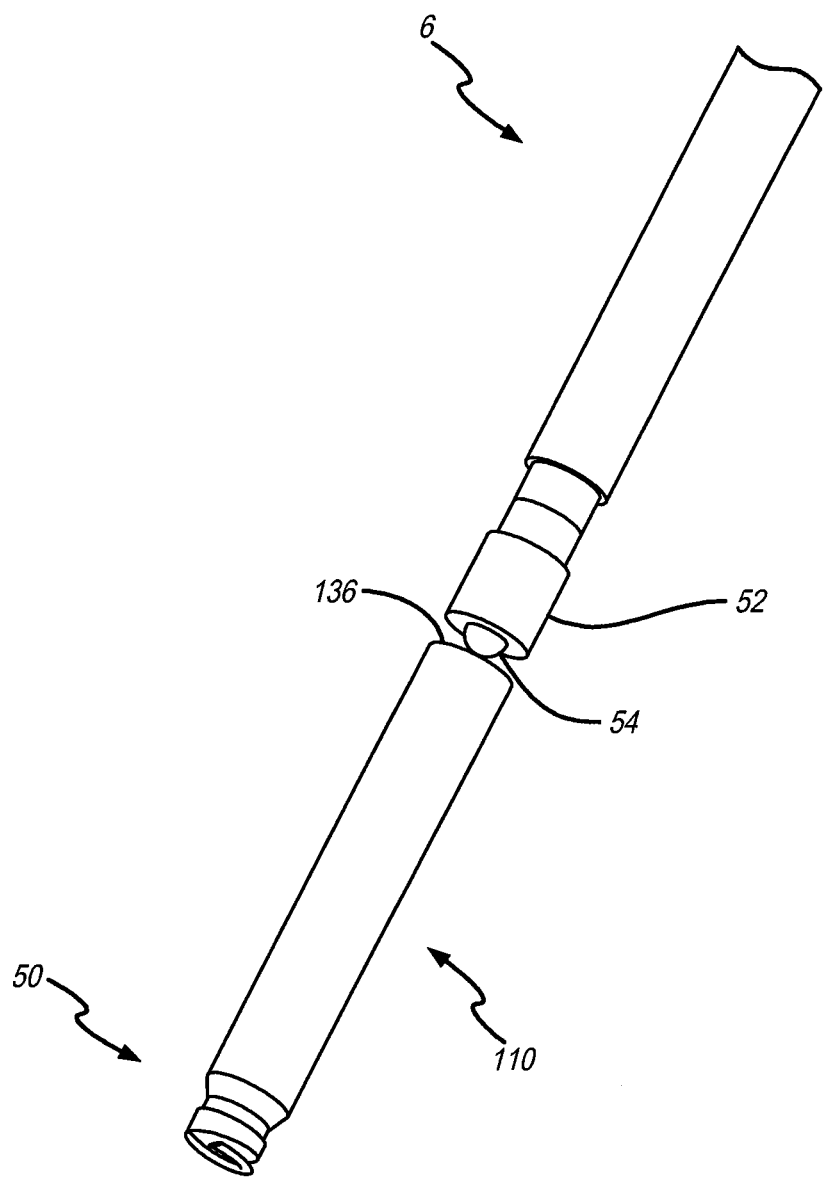
FIG. 1C illustrate an enlarged view of the distal portion of the delivery system.

FIG. 1C illustrate an enlarged view of the distal portion 50 of the delivery system 6. The distal portion 50 includes a female docking cup 52 on the distal end. The docking cup 52 includes a receptacle 54 that is shaped and dimensioned to mate with a male docking surface 136 on the LIMD 110.

Figure 2:
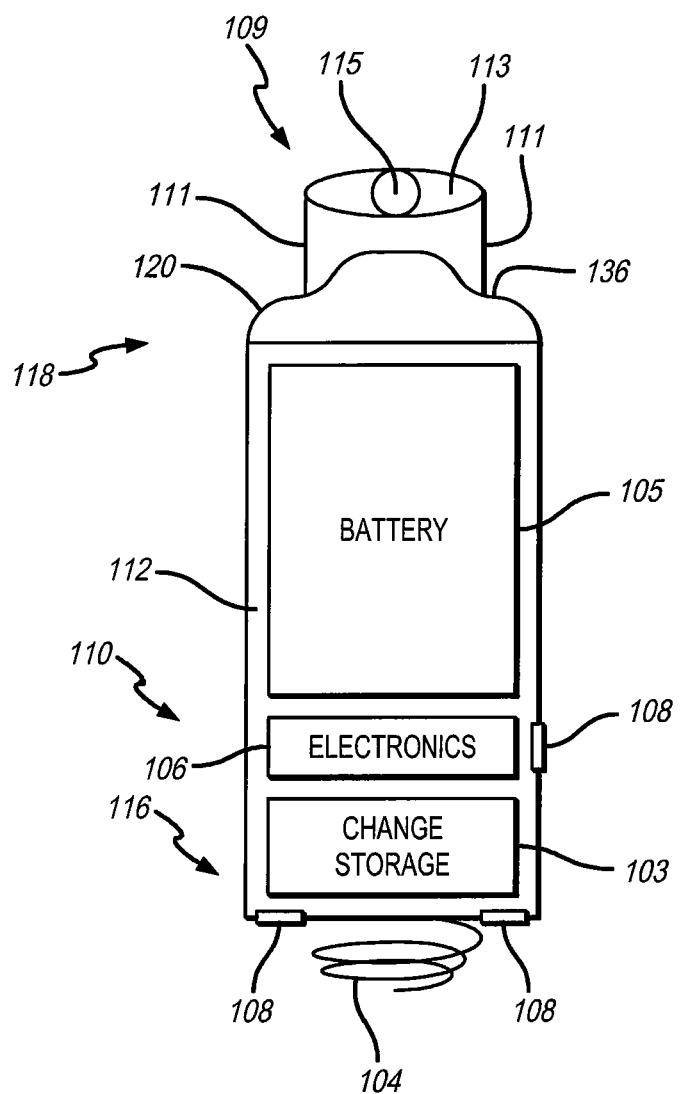
FIG. 2 illustrates a side sectional view of the LIMD formed in accordance with an embodiment herein.

FIG. 2 illustrates a side sectional view of the LIMD 110 formed in accordance with an embodiment herein. The LIMD 110 includes a hermetically sealed housing 112 having a distal portion 116 and a proximal portion 118. One or more electrodes 108 are disposed on the housing 112 in various locations, such as along the distal portion 116. A battery 105, change storage components 103 and electronics package 106 and are disposed within the housing 112. The electronics package 106 is configured to perform various operations associated with an implantable medical device such as, but not limited to, indicating with an external device, sensing cardiac signals detected at one or more electrodes 108, analyzing the cardiac signals for arrhythmias and other physiologic features of interest, as well as controlling generation and delivery of stimulation signals to the electrode or electrodes 108. A fixation mechanism 104 is disposed on the distal portion 116 of the housing 112. The fixation mechanism 104 may be constructed in various manners. For example, the fixation mechanism 104 may represent a helix that is configured to be screwed into tissue of interest when the LIMD 110 is rotated in an appropriate direction. The fixation mechanism 104 may be detached from the tissue of interest by reversing the direction of rotation, such as during explant.

An over torque mechanism 120 is provided on the proximal portion of 118 of the housing 112. The over torque mechanism 120 includes a docking surface 136 having one or more features (e.g., notches, channels, ribs) that are shaped and dimensioned to matt securely with matching reverse features on a docking cap located on a distal end of the delivery tool.

A tether assembly 109 is mounted on, and projects outward from the over torque mechanism 120. The tether assembly 109 includes a pair of flexible cables 111 connected to the torque mechanism 120. The cables 111 are joined to a cross bar 113 that has an opening 115 through the cross bar 113. During implant a tether cable extends through the opening 115 and locking features on the end of the tether cable expand to prevent passage through the opening 115. The locking features are collapsed to release the tether cable from the LIMD 110.

Figure 3:
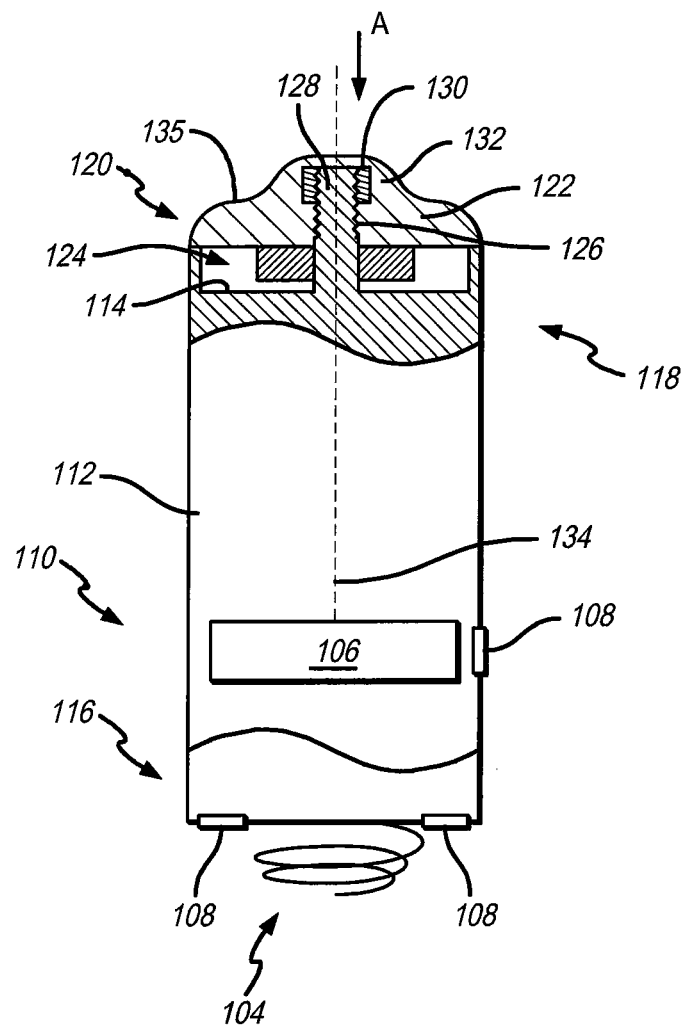
FIG. 3 illustrates a side cross-sectional view of the proximal end portion of the LIMD formed in accordance with an embodiment herein.

FIG. 3 illustrates a side cross-sectional view of the proximal end portion 118 of the LIMD 110 formed in accordance with an embodiment herein. The housing 112 has a proximal end surface 114 that is configured to receive the torque mechanism 120. The torque mechanism 120 includes upper and lower elements, namely a tool engagement element 122 and a torque limiter 124. The tool engagement element 122 is movably coupled to the housing 112. By way of example in one embodiment, the tool engagement element 122 may include a core opening 126 that rotatably fits onto a post 128. A bearing assembly 130 is mounted on the post 128 and fits within end cap 132 which forms part of the tool engagement element 122. The end cap 132 (and tool engagement element 122) rotate about a longitudinal axis 134 of the LIMD 110 and post 128. The bearing assembly 130 rotatably supports the tool engagement element 122 to resist end loading pressure from a direction of arrow a, such as impose by an implant tool catheter.

The tool engagement element 122 includes the male docking surface 136 that is configured to be securely received within a receptacle (docking cap) on a mating delivery tool/catheter. When the receptacle of the delivery tool/catheter engages the docking surface 136, the rotational force may be applied by the tool, such as during implant and explant. A non-rotational secure engagement is maintained between the docking surface 136 and corresponding mating features in the distal end of the delivery tool/catheter by pulling on a tethering cable that is connected to the proximal end of the LIMD. The tethering cable may extend along a lumen within the catheter. By pulling on the tethered cable, the docking surface 136 is held securely against the distal end of the catheter. While maintaining tension on the tethered cable, a physician may rotate a proximal end of the catheter, thereby applying a rotational force through the torque mechanism 120 and causing the LIMD 110 (and fixation mechanism) to rotate in the same direction.

The torque limiter 124 maintains a fixed relation between the tool engagement element 122 and the housing 112 when the torque limiter 124 is in the engaged state. The torque limiter 124 changes from the engaged state to a disengaged state when the rotational force applied to the tool engagement element 122 exceeds a predetermined torque limit. The predetermined torque limit corresponds to a predetermined amount of rotational force sufficient to securely affix the fixation mechanism 104 of the LIMD 110 to tissue of interest without damaging the tissue of interest. It is recognized that the predetermined torque limit may be varied based upon the type of LIMD 110, the construction of the fixation mechanism, the intended location for implant, as well as other characteristics of the device and tissue of interest.

When the rotational force applied to the tool engagement element 122 exceeds the predetermined torque limit, the torque limiter 124 transitions to the disengaged state. When in the disengaged state, the torque limiter 124 allows rotation between the tool engagement element 122 and the housing 112.

Figure 4A:
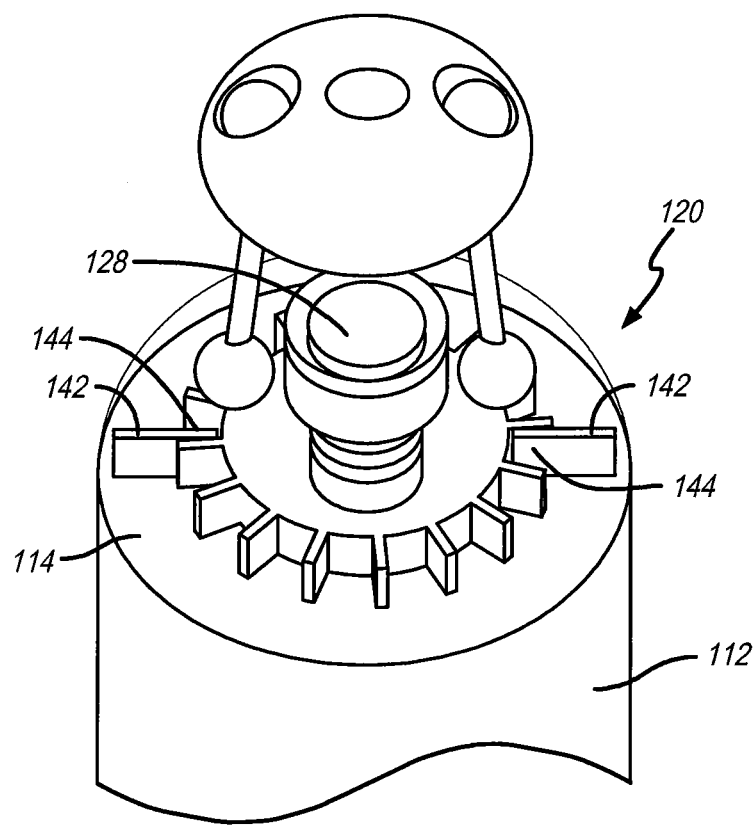
FIG. 4A illustrates a side perspective view of the proximal portion of an LIMD when the torque mechanism is in an engaged state.
Figure 4B:
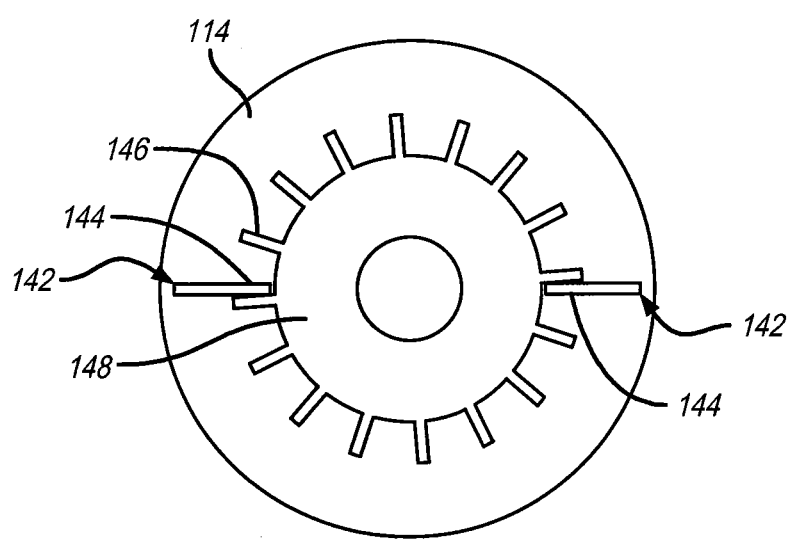
FIG. 4B represent top end views of the torque mechanism (with the tool engagement element removed) while in the engaged state.
Figure 5A:
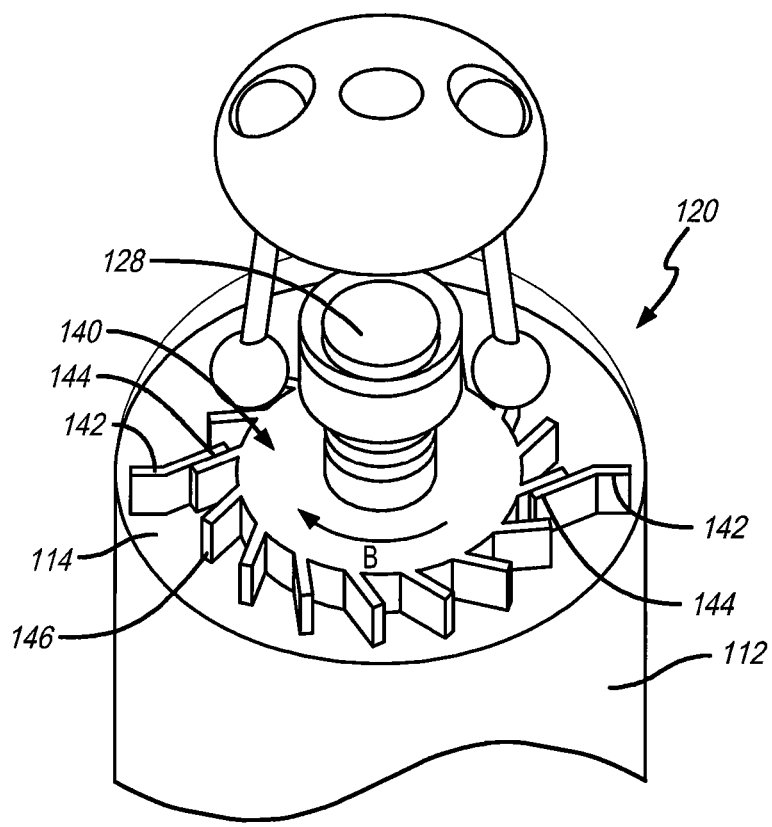
FIG. 5A illustrates a side perspective view of the proximal portion of the LIMD when the torque mechanism is in a disengaged state.
Figure 5B:
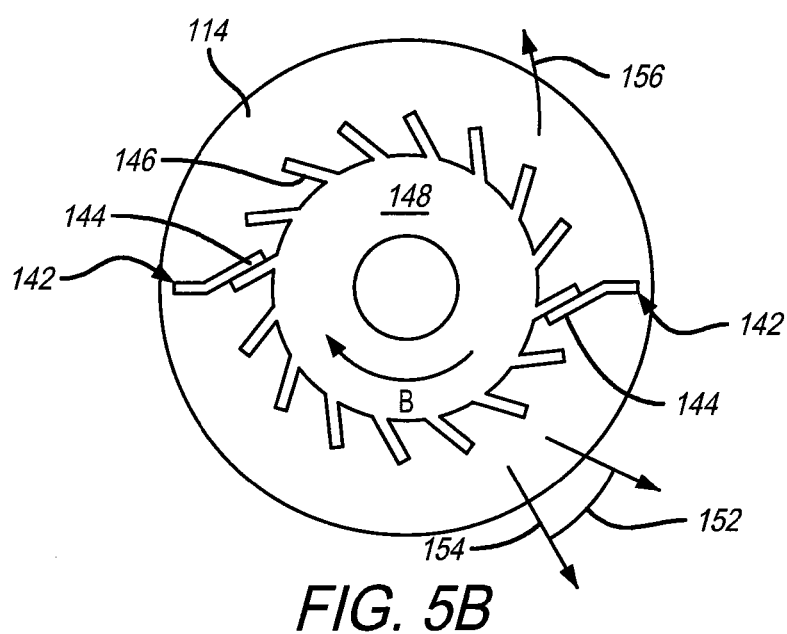
FIG. 5B represent top end views of the torque mechanism (with the tool engagement element removed) while in the disengaged state.

Next, the operation of the torque mechanism 120 is described in connection with FIGS. 4A, 4B, 5A and 5B. FIG. 4A illustrates a side perspective view of the proximal portion of an LIMD 110 when the torque mechanism 120 is in an engaged state. FIG. 5A illustrates a side perspective view of the proximal portion of the LIMD 110 when the torque mechanism 120 is in a disengaged state. FIGS. 4A and 5A show the tool engagement element 122 in a shadow format in order that the underlying components are visible. FIGS. 4B and 5B represent top end views of the torque mechanism 120 (with the tool engagement element 122 removed) while in the engaged state and disengaged state, respectively.

In FIGS. 4A and 5A, the torque mechanism 120 includes a base member 140 securely affixed to the proximal end surface 114 of the housing 112. The post 128 is illustrated to extend outward in a proximal direction (along the longitudinal axis 134) from the base member 140. By way of example, the base member 140 may be constructed as a gear having ratchet teeth 146 evenly distributed about a perimeter of a body portion 148 of the gear. The torque limiter 124, is configured as spring arms 142, that fixedly engage the ratchet teeth 146 when in the engaged state (as illustrated in FIGS. 4A and 4B). FIGS. 4A and 5A illustrates an embodiment for the torque limiter 124, representing a pair of spring arm 142 securely mounted to the tool engagement member 122. The spring arm 142 includes active ends 144 that extend inward toward one another to engage the base member 140. When in the engaged state, the spring arms 142 includes active ends 144 that engage ratchet teeth 146 to prevent relative rotation between the tool engagement member 122 and the housing 112. The spring arms 142 and ratchet teeth 146 interact to establish the predetermined torque limit at which the torque limiter 124 changes from the engaged state to the disengaged state. By way of example, the predetermined torque limit is controlled and changed by constructing the spring arms 142 and base member 140 from predetermined materials, with predetermined dimensions, thicknesses, slopes and spacings relative to one another.

When a rotational force is applied that exceeds the predetermined torque limit the spring arms 142 bend or otherwise flex, as illustrated in FIGS. 5A and 5B thereby permitting the base member 142 to rotate in the direction of arrow B. In the event that excessive rotational force continues to be applied, the active ends 144 permit currently engaged ratchet teeth 146 to pass the spring arms 142 after which, the spring arms 142 engage the next successive ratchet teeth 146. As the spring arms 142 flex and pass over successive ratchet teeth, the torque limiter 124 releases the tool engagement element 122 and permits rotation of the tool engagement element 122 relative to the base member 140 thereby maintaining a releasable interconnection between the tool engagement element 122 and the base member 140 when in the engaged and disengaged states.

In the example of FIGS. 4A-4B and 5A-5B, the ratchet teeth 146 are formed with sloped surfaces. As illustrated in FIG. 5B, the sloped surfaces of the ratchet teeth 146 form an acute angle 152 relative to a radius 154 of the gear body 148. The sloped surfaces extend radially outward from a center of the gear body 148 and curve, such as in the direction of arrow 156 towards a direction of rotational movement of the tool engagement element 122 when in the disengaged state. Stated from another perspective, the sloped surfaces (corresponding to arrow 156) curve in a direction corresponding to the direction in which rotational force is applied by the delivery tool, which also corresponds to the direction in which the fixation mechanism is rotated to become securely affixed to tissue of interest.

FIGS. 4A and 5A illustrates an embodiment for the torque limiter 124, representing a pair of spring arm 142 securely mounted to the tool engagement member 122. The spring arm 142 includes active ends 144 that extend inward toward one another to engage the base member 140.

As explained in connection with FIGS. 4A-4B and 5A-5B, the spring arm 142 to maintains the fixed relation between the tool engagement element 122 in the base member 140 when in the engaged state. The spring arm 142 snappably releases the base member 140 when transitioning from the engaged state to the disengaged state in response to rotational force that exceeds the predetermined torque limit.

The configuration illustrated in FIGS. 4A-4B and 5A-5B may be reversed. For example, the spring arms 142 may be securely affixed to the base member 140 and project radially outward from the base member 140. The ratchet teeth 146 may be provided on the tool engagement element 122 and positioned circumferentially around the base member. In this alternative example, the spring arms 142 would project radially outward, with active ends 144 extending radially outward and engaging ratchet teeth formed on the tool engagement element 142. The spring arms 142 would transition between engage states and disengaged states, as explained above, when a rotational force was applied to the LIMD 110 that exceeds the predetermined torque limit.

Figure 6:
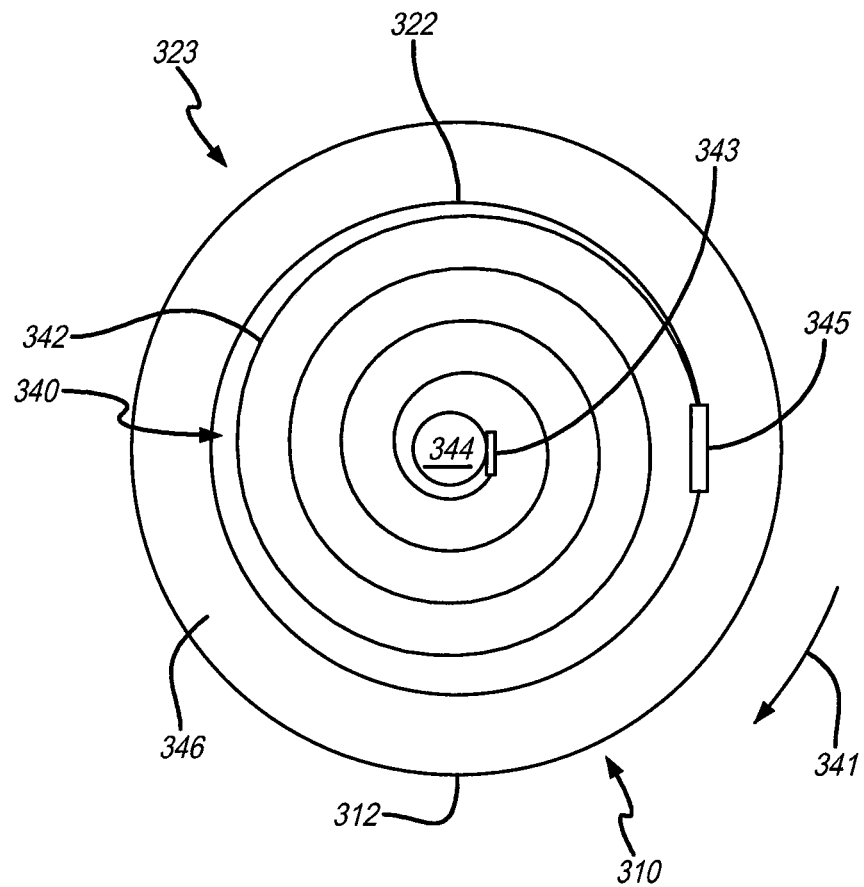
FIG. 6 illustrates a top view of a torque mechanism formed in accordance with an alternative embodiment.

FIG. 6 illustrates a top view of a torque mechanism 320 formed in accordance with an alternative embodiment. The torque mechanism 320 includes a base element 340 that represents a spiral shaped spring 342 having a first interior end 343 that is attached to a post 344 extending upward from the proximal end 346 of the LIMD 310. The spring 342 includes an exterior end 345 that is attached to a tool engagement element 322. The spiral shaped spring 342 maintains an initial shape having an initial spacing between each turn of the spiral when in the engaged state. When in the initial shape, corresponding to the engaged state, the spring 342 transfers a fixed amount of rotational motion (e.g. all rotational motion) from the tool engagement element 322 to the housing 312 of the LIMD 310 when rotational force is applied to the tool engagement element 322. The spring 342 changes to the disengaged state when a rotational force is applied that exceeds the predetermined torque limit. When changing to the disengaged state, the turns of the spring 342 change the relative spacing there between, such that the relative positions of the interior and exterior ends 343 and 345 change with respect to one another. For example, the exterior end 345 may move in a circumferential direction of arrow 341 when a rotational force is applied that exceeds the predetermined torque limit.

Figure 7:
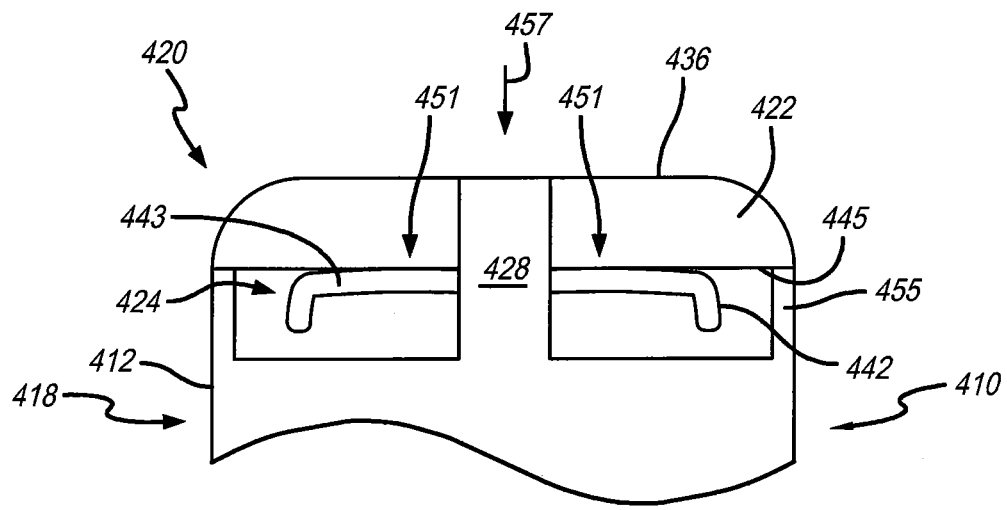
FIG. 7 illustrates a side view of a proximal portion of an LIMD that includes a torque mechanism that is formed in accordance with an alternative embodiment.

FIG. 7 illustrates a side view of a proximal portion 418 of an LIMD 410 that includes a torque mechanism 420 that is formed in accordance with an alternative embodiment. The torque mechanism 420 includes a tool engagement element 422 having a docking surface 436 that is configured to securely mate with a receptacle of a delivery tool as explained herein. The tool engagement element 422 is rotatably mounted on a post 428 that extends upward from a proximal end of the housing 412. A torque limiter 424 is constructed to include a friction spring 442 is securely and non-rotationally mounted to the post 428. The friction spring 442 includes one or more lateral arms 443 that extend radially outward from the post 428 and are positioned immediately adjacent and in abutting relation with a lower engaging surface 445 (also referred to as a torque limiter engaging surface) on the tool engagement element 422.

During implant, the receptacle of a delivery tool engages the docking surface 436 and induces rotational force onto the tool engagement element 422. As the tool engagement element 422 begins to rotate, a friction interface is maintained (in areas 451) between the surface 445 and arms 443 of the spring 442. As the tool engagement element 422 is rotated, the frictional interface at 451 transfers the rotational force to the spring 442 thereby inducing a similar rotational force into the LIMD 410 at the post 428. The frictional interface at 451 defines the predetermined torque limit. When the rotational force induced at the tool engagement element 422 exceeds the predetermined torque limit, the lower surface 445 rotates relative to the arms 443.

Optionally, a shroud 455 may be provided as part of the housing 412 and extend to a point substantially adjacent to the surface 445 of the tool engagement element 422. The shroud 455 may define an amount by which the tool engagement element 422 may move toward the housing 422 when experiencing forces in the direction of arrow 457 as applied by a delivery tool.

Optionally, the torque limiter 424 may be constructed as a disk that is mounted on the post 428 and secured to the post 428 such that the disk does not rotate relative to the post 428.

Figure 8:
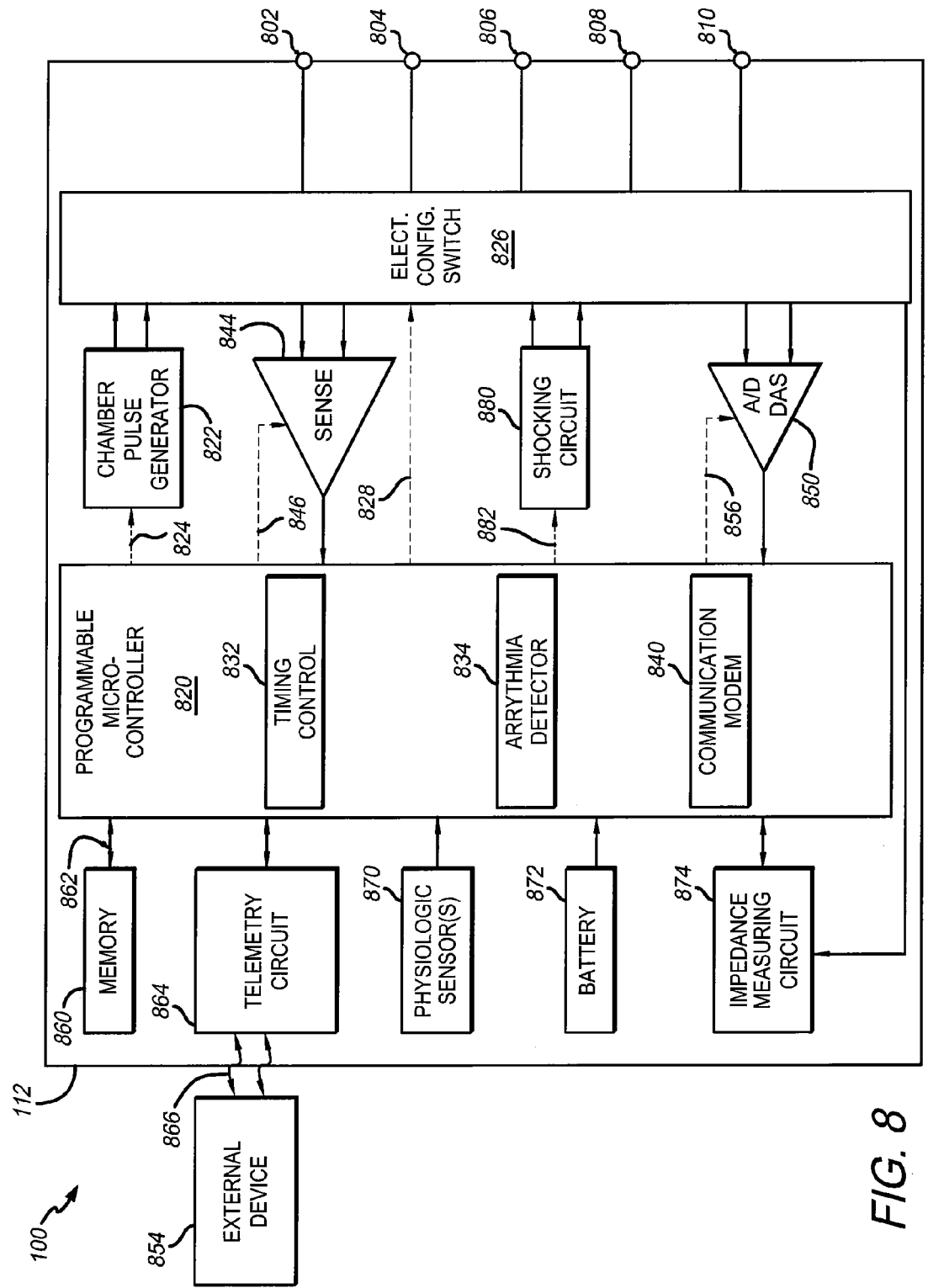
FIG. 8 is a schematic block diagram showing internal components of the LIMD according to an embodiment.

FIG. 8 is a schematic block diagram showing internal components of the LIMD 110 according to an embodiment. In other embodiments, the LIMD 110 may have more or fewer components than are illustrated and described. In addition, in other embodiments, the LIMD 110 may have a different arrangement of the components, such that some components illustrated as two discrete components may be combined into one single component or vice-versa.

The LIMD 110 has a housing 112 to hold the electronic/computing components. The housing 112 (which is often referred to as the "can", "case", "encasing", or "case electrode") may be programmably selected to act as the return electrode for certain stimulus modes. Housing 112 further includes a plurality of terminals 802, 804, 806, 808, 810 that interface with electrodes of the LIMD 110. Since the LIMD 110 is leadless, the terminals 802-810 may be located at or at least proximate to the electrodes, which are disposed on or extend from the housing 112.

The LIMD 110 includes a programmable microcontroller 820 that controls various operations of the LIMD 110, including cardiac monitoring and stimulation therapy. Microcontroller 820 includes a microprocessor (or equivalent control circuitry), RAM and/or ROM memory, logic and timing circuitry, state machine circuitry, and I/O circuitry. The microcontroller 820 may be or include the processor. The microcontroller 820 includes the ability to process or monitor input signals (data) as controlled by a program code stored in a designated block of memory. The details of the design and operation of the microcontroller 820 are not critical to the invention, and any suitable microcontroller 820 may be used that carries out the functions described herein.

Microcontroller 820 is illustrated as including timing control circuitry 832 to control the timing of the stimulation energy or pulses (e.g., pacing rate, atrio-ventricular (AV) delay etc.). The timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions. Although not shown, the microcontroller 820 may further include other dedicated circuitry and/or firmware/software components that assist in monitoring various conditions of the patient's heart and managing pacing therapies.

The LIMD 110 further includes a pulse generator 822 that generates stimulation pulses for delivery by one or more electrodes coupled thereto. The pulse generator 822 is controlled by the microcontroller 820 via control signals 824. The pulse generator 822 is coupled to the select electrode(s) via the electrode configuration switch 826. The switch 826 is controlled by control signals 828 from a microcontroller 820. Although only a single pulse generator 822 is illustrated in FIG. 8, optionally the LIMD 110 may include multiple pulse generators similar to pulse generator 822, and each pulse generator may be coupled to one or more electrodes and controlled by the microcontroller 820 to deliver select stimulus pulse(s) to the corresponding one or more electrodes.

The LIMD 110 includes a sensing circuit 844 selectively coupled to one or more electrodes through the switch 826. The sensing circuit 844 detects the presence of cardiac activity in certain chambers of the heart. The sensing circuit 844 may include dedicated sense amplifiers, multiplexed amplifiers, or shared amplifiers. It may further employ one or more low power, precision amplifiers with programmable gain and/or automatic gain control, band pass filtering, and threshold detection circuit to selectively sense the cardiac signal of interest. The automatic gain control enables the sensing circuit 844 to sense low amplitude signals. Switch 826 determines the sensing polarity of the cardiac signal by selectively closing the appropriate switches. In this way, the clinician may program the sensing polarity independent of the stimulation polarity.

The output of the sensing circuit 844 is connected to the microcontroller 820 which, in turn, triggers or inhibits the pulse generator 822 in response to the absence or presence of cardiac activity. The sensing circuit 844 receives a control signal 846 from the microcontroller 820 for purposes of controlling the gain, threshold, polarization charge removal circuitry (not shown), and the timing of any blocking circuitry (not shown) coupled to the inputs of the sensing circuitry. Although only a single sensing circuit 844 is illustrated in FIG. 8, optionally the LIMD 110 may include multiple sensing circuits, similar to sensing circuit 844. Each sensing circuit may be coupled to one or more electrodes and controlled by the microcontroller 820 to sense electrical activity detected at the corresponding one or more electrodes. The sensing circuit 844 may operate in a unipolar sensing configuration or in a bipolar sensing configuration.

The LIMD 110 further includes an analog-to-digital (ND) data acquisition system (DAS) 850 coupled to one or more electrodes via the switch 826 to sample cardiac signals across any pair of desired electrodes. The data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). The data acquisition system 850 is controlled by a control signal 856 from the microcontroller 820.

The microcontroller 820 is coupled to a memory 860 by a suitable data/address bus 862. The programmable operating parameters used by the microcontroller 820 are stored in memory 860 and used to customize the operation of the LIMD 110 to suit the needs of a particular patient. Such operating parameters define, for example, pacing pulse amplitude, pulse duration, electrode polarity, rate, sensitivity, automatic features, arrhythmia detection criteria, and the amplitude, waveform, and vector of each shocking pulse to be delivered to the patient's heart within each respective tier of therapy.

The operating parameters of the LIMD 110 may be non-invasively programmed into the memory 860 through a telemetry circuit 864 in telemetric communication via communication link 866 with the external device 854. The telemetry circuit 864 allows intracardiac electrograms and status information relating to the operation of the LIMD 110 (as contained in the microcontroller 820 or memory 860) to be sent to the external device 854 through the established communication link 866.

The LIMD 110 can further include magnet detection circuitry (not shown) coupled to the microcontroller 820, to detect when a magnet is placed over the device. A magnet may be used by a clinician to perform various test functions of the LIMD 110 and/or to signal the microcontroller 820 that the external programmer 854 is in place to receive or transmit data to the microcontroller 820 through the telemetry circuits 864.

The LIMD 110 may be equipped with a communication modem (modulator/demodulator) 840 to enable wireless communication with a remote device, such as a second implanted LIMD in a master/slave arrangement, such as described in U.S. Pat. No. 7,630,767. The communication modem 840 may be implemented in hardware as part of the microcontroller 820, or as software/firmware instructions programmed into and executed by the microcontroller 820.

Alternatively, the modem 840 may reside separately from the microcontroller 820 as a standalone component.

The LIMD 110 can further include one or more physiologic sensors 870. Such sensors are commonly referred to as "rate-responsive" sensors because they are typically used to adjust pacing stimulation rates according to the exercise state of the patient. However, the physiological sensor 870 may further be used to detect changes in cardiac output, changes in the physiological condition of the heart, or diurnal changes in activity (e.g., detecting sleep and wake states). Signals generated by the physiological sensors 870 are passed to the microcontroller 820 for analysis. The microcontroller 820 responds by adjusting the various pacing parameters (such as rate, AV Delay, V-V Delay, etc.) at which the atrial and/or ventricular pacing pulses are administered. While shown as being included within the LIMD 110, the physiologic sensor(s) 870 may be external to the LIMD 110, yet still be implanted within or carried by the patient. Examples of physiologic sensors might include sensors that, for example, sense respiration rate, pH of blood, ventricular gradient, activity, position/posture, temperature, minute ventilation, and so forth.

A battery 872 provides operating power to all of the components in the LIMD 110. The battery 872 is capable of operating at low current drains for long periods of time, and is capable of providing high-current pulses (for capacitor charging) when the patient requires a shock pulse. For example, the battery 872 may be configured to provide pulses in excess of 2 amps at voltages above 2 volts for periods of 10 seconds or more. The battery 872 may also have a predictable discharge characteristic so that elective replacement time can be detected. As one example, the LIMD 110 includes lithium/silver vanadium oxide batteries.

The LIMD 110 further includes an impedance measuring circuit 874. The impedance measuring circuit 874 may be used for impedance surveillance during the acute and chronic phases for proper LIMD 110 positioning or dislodgement. The impedance measuring circuit 874 may also be used for detecting, such as detecting operable electrodes and automatically switching to an operable pair if dislodgement occurs, detecting when the LIMD 110 has been implanted, and detecting the opening of heart valves. Furthermore, the impedance measuring circuit 874 may be used for measuring, such as measuring respiration or minute ventilation, measuring thoracic impedance, measuring stroke volume, and the like. The impedance measuring circuit 874 is coupled to the switch 826 so that the impedance measuring circuit 874 may use any desired electrode.

The LIMD 110 may further include a shocking circuit 880, which is controlled by the microcontroller 820 by way of control signals 882. The shocking circuit 880 generates shocking pulses of low (e.g., up to 0.5 joules), moderate (e.g., 0.5-10 joules), or high energy (e.g., 10 to 40 joules), as controlled by the microcontroller 820. Such shocking pulses are applied to the patient's heart through shocking electrodes, if available on the LIMD 110. It is noted that the shock therapy circuitry is optional and may not be implemented in the LIMD 110, as the various embodiments described above and further below may not be configured to deliver high voltage shock pulses. On the other hand, it should be recognized that the LIMD 110 may be used within a system that includes backup shock capabilities, and hence such shock therapy circuitry may be included in the LIMD 110.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A leadless implantable medical device (LIMD), comprising:
 a hermetic housing having a distal portion and a proximal portion;
 an electrode proximate to the distal portion;
 an electronics package disposed in the housing, the electronics package configured to generate and deliver stimulation signals to the electrode;
 a fixation mechanism disposed on the distal portion of the housing; and
 a torque mechanism disposed on the proximal portion of the housing, the torque mechanism having a tool engagement element movably coupled to the housing, the tool engagement element having a rotational force applied thereto during implant, the torque mechanism including a torque limiter that maintains a fixed relation between the tool engagement element and the housing when in an engaged state, the torque limiter changing from the engaged state to a disengaged state when the rotational force exceeds a predetermined torque limit.

2. The LIMD of claim 1, wherein the torque limiter allows rotation between the tool engagement element and the housing when the torque limiter is in the disengaged state.

3. The LIMD of claim 1, wherein the torque mechanism includes a base member securely affixed to a proximal end of the housing and a post extending outward in a proximal direction from the base member, the tool engagement member rotatably mounted on the post, the torque limiter releasable interconnecting the tool engagement element and the base member when in the engaged and disengaged states.

4. The LIMD of claim 3, wherein the base member represents a gear having ratchet teeth positioned about a perimeter of the gear, the torque limiter fixably engaging the ratchet teeth, when in the engaged state, to prevent relative rotation between the tool engagement member and the housing.

5. The LIMD of claim 4, wherein the torque limiter engages a sloped surface of the ratchet teeth, where the sloped surface forms an acute angle relative to a radius of the gear, the sloped surfaces extending radially outward from a center of the gear and curving towards a direction of rotational movement of the torque limiter when in the disengaged state in which the torque limiter rotates with the tool engagement element about the gear.

6. The LIMD of claim 1, wherein the torque mechanism includes a base member securely affixed to a proximal end of the housing, wherein the torque limiter represents a spring arm securely mounted to one of the tool engagement member and base member, the spring arm maintaining the fixed relation between the tool engagement element and base member when in the engaged state, the spring arm snappably releasing another of the tool engagement member and the base member when transitioning from the engaged state to the disengaged state in response to the rotational force exceeding the predetermined torque limit.

7. The LIMD of claim 1, wherein the predetermined torque limit corresponds to an amount of rotational force sufficient to securely affix the fixation mechanism on the distal portion of the housing to tissue of interest, without damaging the tissue of interest.

8. The LIMD of claim 1, wherein the tool engagement element includes a male docking surface shaped and dimensioned to securely engage a distal end of a delivery tool such that the delivery tool applies the rotational force thereby causing the fixation mechanism to rotate and securely engage the tissue of interest.

9. The LIMD of claim 1, wherein the torque limiter constitutes a spiral shaped spring having a first end attached to the tool engagement element and a second end attached to the housing, the spiral shaped spring maintaining an initial shape when in the engaged state to transfer a fixed amount of motion from the tool engagement element to the housing when the rotational force is applied, the spiral shaped spring changing shape when in the disengaged state.

10. The LIMD of claim 1, wherein the tool engagement element is rotatably mounted on a post extending from the proximal end of the housing, the tool engagement element including an interior surface, the torque limiter representing a spring fixedly mounted to the housing and located between the interior surface of the tool engagement element and a proximal end of the housing, the spring and interior surface frictionally engaging one another to prevent relative rotation there between when in the engaged state.

11. A method for providing a leadless implantable medical device (LIMD), the method comprising:
providing a hermetic housing having a distal portion and a proximal portion, where an electrode is located proximate to the distal portion, an electronics package is disposed in the housing, and a fixation mechanism is disposed on the distal portion of the housing; and
disposing a torque mechanism on the proximal portion of the housing, the torque mechanism including a tool engagement element movably coupled to the housing;
applying a rotational force to the tool engagement element during implant;
maintaining the torque mechanism in an engaged state, in which the tool engagement element and the housing remain in a fixed relation with respect to one another, when the rotational force is at or below a predetermined torque limit; and
changing the torque mechanism to a disengaged state, in which the tool engagement element rotates relative to the housing, when the rotational force exceeds the predetermined torque limit.

12. The method of claim 11, further comprising providing a torque limiter, in the torque mechanism, that allows rotation between the tool engagement element and the housing when the torque limiter is in the disengaged state.

13. The method of claim 11, wherein the torque mechanism includes a base member securely affixed to a proximal end of the housing, the method comprising releasable interconnecting the tool engagement element and the base member when in the engaged and disengaged states.

14. The method of claim 13, wherein the base member represents a gear having ratchet teeth positioned about a perimeter of the gear, the method comprising preventing relative rotation between the tool engagement member and the housing by fixably engaging the ratchet teeth when in the engaged state.

15. The method of claim 11, wherein the predetermined torque limit corresponds to an amount of rotational force sufficient to securely affix the fixation mechanism on the distal portion of the housing to the tissue of interest, without damaging the tissue of interest.

16. The method of claim 11, further comprising securely engaging a docking surface on the tool engagement element with a distal end of a delivery tool and applying the rotational force through the delivery tool to cause the fixation mechanism to rotate and securely engage the tissue of interest.

* * * * *